US007297686B2

(12) United States Patent
Hwang et al.

(10) Patent No.: US 7,297,686 B2
(45) Date of Patent: Nov. 20, 2007

(54) CHROMIUM COMPLEX WITH INSULIN-LIKE ACTIVITY

(76) Inventors: David L. Hwang, 1207 S. 9th Ave., Arcadia, CA (US) 91006; Bingrong Liu, 3191 Sepulveda Blvd., #308, Los Angeles, CA (US) 90034

(*) Notice: Subject to any disclaimer, the term of this patent is extended or adjusted under 35 U.S.C. 154(b) by 503 days.

(21) Appl. No.: 11/022,205

(22) Filed: Dec. 23, 2004

(65) Prior Publication Data

US 2006/0105984 A1 May 18, 2006

Related U.S. Application Data

(60) Provisional application No. 60/628,802, filed on Nov. 16, 2004.

(51) Int. Cl.
*A01N 43/04* (2006.01)
*A61K 31/70* (2006.01)
*A01N 55/02* (2006.01)
*A61K 31/28* (2006.01)

(52) U.S. Cl. .................. 514/47; 514/43; 514/45; 514/46

(58) Field of Classification Search ............ None
See application file for complete search history.

(56) References Cited

U.S. PATENT DOCUMENTS

| | | | | |
|---|---|---|---|---|
| 3,925,433 | A | 12/1975 | Abdel-Monem et al. | 260/438.5 |
| 4,242,257 | A | 12/1980 | Silio | 260/112.5 |
| 4,923,855 | A | 5/1990 | Jensen | 514/188 |
| 5,872,102 | A | 2/1999 | Vincent et al. | 514/21 |
| 5,969,116 | A | 10/1999 | Martin | 536/22.1 |
| 6,258,848 | B1 | 7/2001 | Fantus | 514/562 |
| 6,365,176 | B1 | 4/2002 | Bell et al. | 424/439 |
| 6,444,231 | B2 | 9/2002 | Vincent et al. | 424/655 |
| 6,689,383 | B1 | 2/2004 | Anderson et al. | 424/464 |
| 6,689,385 | B2 | 2/2004 | Richardson et al. | 424/464 |
| 6,713,469 | B2 | 3/2004 | de la Harpe et al. | 514/188 |
| 6,809,115 | B2 | 10/2004 | Katz et al. | 514/505 |

OTHER PUBLICATIONS

Bossard et al. Journal of Biological Chemistry (1981), vol. 256, pp. 6617-6622.*
*A Glucose Tolerance Factor and its Differentiation from Factor 3*, K. Schwarz; W. Mertz, Arch. Biochem. Biophys. 72:515-518, 1957.
*Chromium (III) and the Glucose Tolerance Factor*, K. Schwarz; W. Mertz, Arch. Biochem. Biophys. 85:292-295, 1959.
*The bioinorganic chemistry of chromium (III)*, J.B. Vincent, Polyhedron, 20:1-26, 2001.
*Recent advances in the nutritional biochemistry of trivalent chromium*, J.B. Vincent, Proceedings of the Nutrition Society, 63:41-47, 2004.
*Present knowledge of the role of chromium*, W. Mertz; E.W. Toepfer; E.E. Roginski; M.M. Polansky; Fed. Proc. 33:2275-2280, 1974.

*On the nature of the glucose tolerance factor from yeast*, T. Urcemow; O.H. Wieland, Horm. Metab. Res. Suppl. 16:51-54, 1984.
*Extracts of brewer's yeast contain gaba which enhances activation fo glycogen synthetase by insulin in isolated rat hepatocytes*, E.S. Holdsworth; E. Neville, Biochem. Int. 17:1107-1116, 1988.
*Effects of extracts of high-and low-chromium brewer's yeast on metabolism of glucose by hepatocytes from rats fed on high-or low-Cr diets*, E.S. Holdsworth; E. Neville, British Journal of Nutrition, 63: 623-630, 1990.
*A fraction derived from brewer's yeast inhibits cholesterol synthesis by rat liver preparations* in vitro, E.S. Holdsworth; D.V. Kaufman; E. Neville, British Journal of Nutrition, 65:285-299, 1991.
*Isolation of a biologically active low-molecular-mass chromium compound from rabbit liver*, A. Yamamoto; O. Wada; T. Ono, Eur. J. Biochem, 165:627-631, 1987.
*Evidence that chromium is an essential factor for biological activity of low-molecular-weight, chromium-binding substance*, A. Yamamoto; O. Wada; S. Wanabe, Biochem. Biophys. Res. Comm. 163:189-193, 1989.
*Is glucose tolerance factor an artifact produced by acid hydrolysis of low-molecular-weight chromium-binding substance?*, K.H. Sumrall; J.B. Vincet, Polyhedron 16:4171-4177, 1997.
*A biologically active form of chromium may activate a membrane phosphotyrosine Phosphatase (PTP)*, C.M. Davis; K.H. Sumrall; J.B. Vincent, Biochemistry 35:12963-12969, 1996.
*Chromium Oligopeptide Activates Insulin Receptor Tyrosine Kinase Activity*, C.M. Davis; J.B. Vincent, Biochemistry 36:4382-4385, 1997.
*Isolation and chracterization of a biologically active chromium oligopeptide from bovine liver*, C.M. Davis; J.B. Vincent, Arch. Biochem. Biophys. 339:335-343, 1997.
*Composition and biological activity of chromium-pyridine carboxylate complexes*, G.W. Evans, Int. J. Biosocial Med. And Res. 11:163-180, 1989.
*The biomimetic [Cr3O(O2CCH2CH3)6(H2O)3]+ decreases plasma cholesterol and triglycerides in rates: towards chromium-continaing therapeutics*, Y. Sun; K. Mallya; J. Ramirez; J.B. Vincent, J. Biol. Inorg. Chem. 4:838-845, 1999.
*The biomimetic [Cr3O(O2CCH2CH3)6(H2O)3]+ decreases plasma insulin, cholesterol, and triglycerides in healthy and type II diabetic rats but not type I diabetic rats*, Y. Sun; B.J. Clodfelder, A.A. Shute, T. Irvin; J.B. Vincent, J. Biol. Inorg. Chem. 7:852-862, 2002.
*Insulin-like activity of chromium-binding fractions from brewer's yeast*, D.L. Hwang; Y-C Tay; A. Lev-Ran, Biochimica et Biophysica Acta. 882:331-336, 1986.
*Chromium-associate 32 P-labeling of proteins*, D.L. Hwang; A. Lev-Ran; T. Papoian; W.K. Beech, J. Inorg. Biochem. 30:219-225, 1987.

* cited by examiner

*Primary Examiner*—Patrick Lewis
(74) *Attorney, Agent, or Firm*—Michael Fedrick; Sheldon Mak Rose & Anderson (57) ABSTRACT

A chromium complex for use in treating metabolic disorders, particularly Type 1 and Type 2 diabetes.

13 Claims, 5 Drawing Sheets

CHROMIUM COMPLEX WITH INSULIN-LIKE ACTIVITY

The present application claims priority from U.S. Provisional Patent Application No. 60/628,802, filed Nov. 16, 2004, entitled "CHROMIUM COMPLEX WITH INSULIN-LIKE ACTIVITY AND METHODS OF MAKING AND USING THE SAME," the entire disclosure of which is hereby incorporated by reference.

BACKGROUND

Chromium is an essential trace element for mammals. Its role in glucose metabolism has been investigated since the discovery in the 1950's of an organic chromium-associated compound, which was given the name glucose tolerance factor (GTF). GTF was derived from brewer's yeast and appeared to have insulin-potentiating activity. However, the chemical structure of GTF has been subject to debate.

A low molecular weight chromium-containing substance with insulin-potentiating activity, termed chromodulin, has also been reported. Chromodulin, which has been isolated from rabbit liver, porcine kidney, bovine colostrum and bovine liver, has been described as an oligopeptide consisting of glutamate, aspartate, glycine and cysteine residues bound to four chromic ions. However, U.S. Pat. No. 6,444,231 to Vincent tested a mixture comprising a 4:2:4:2:2 ratio of chromium, aspartate, glutamate, glycine, and cysteine, and found that this compound did not exhibit the GTF activity seen with chromodulin.

Several clinical studies indicate that chromium supplementation may improve diabetes control. Because of insufficient information on the use of chromium to treat diabetes, however, the U.S. National Institutes of Health has issued no recommendations for dietary chromium supplementation.

SUMMARY

The present invention comprises novel chromium compounds which have insulin-like activity, as well as methods of making and using such compounds. In one aspect, the present invention comprises a method of treating a metabolic disorder by administering a therapeutically effective amount of a pharmaceutical composition that includes a chromium adenosine compound to a subject in need thereof. The chromium adenosine compound is preferably a chromium adenosine phosphate compound, and the adenosine phosphate is preferably AMP, ADP, or ATP. In a preferred embodiment, the chromium adenosine phosphate compound is a complex of chromium, ATP, and cysteine in which the molar ratio of chromium:cysteine:ATP is 1:2:1.

The chromium adenosine compounds can be administered by a number of different routes, such as intravenous administration, intramuscular administration, intraperitoneal administration, subcutaneous administration, and oral administration. The amount of the chromium adenosine compound administered to a subject is preferably between about 50 μg and 120 μg of the compound per kilogram of body weight of the subject. When the chromium adenosine compound is administered orally, the amount of the chromium adenosine compound administered to the subject is preferably between about 2000 μg and 4000 μg. The present compounds can be used in particular to treat metabolic disorders such as Type 1 and Type 2 diabetes.

The present invention further comprises a pharmaceutical composition comprising a chromium adenosine compound for use in treating a metabolic disorder, such as diabetes. The chromium adenosine compound is preferably a chromium adenosine phosphate compound in which the adenosine is AMP, ADP, or ATP. In a preferred embodiment, the chromium adenosine phosphate compound is a complex of chromium, ATP, and cysteine, which preferably has a molar ratio of chromium:cysteine:ATP of 1:2:1. The chromium adenosine compound preferably further includes a pharmaceutically acceptable excipient.

In another embodiment, the present invention comprises a method of treating a metabolic disorder by administering to a subject in need thereof a pharmaceutical composition comprising a therapeutically effective amount of a complex of chromium and either adenine or an adenine derivative. Such a complex can also include further components, such as cysteine.

DRAWINGS

These and other features, aspects and advantages of the present invention will become better understood with regard to the following description, appended claims, and accompanying figures where:

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by their intended use.

DESCRIPTION

Definitions

As used herein, the following terms have the meanings given below, unless a different meaning is clearly intended by the context in which such term is used.

"Adenosine compound" as used herein refers to the nucleic acid adenosine as well as to adenosine derivatives.

"Adenosine derivatives" refers to adenosine compounds that comprise a derivative of adenine and/or a derivative of a ribose, deoxyribose, or dideoxyribose molecule.

"Adenine moiety" refers to an adenine molecule or derivatives thereof linked to another molecule by a linkage at the 9-nitrogen position.

"Adenosine phosphate compound" refers to an adenosine compound in which the 5' carbon of the nucleoside sugar moiety is bound to at least one phosphate group. Phosphate groups can be mono-, di-, or tri-phosphates or derivatives thereof, such as 1-, 2-, and/or 3-thiotriphosphates. The adenosine phosphates used herein are typically adenosine monophosphate ("AMP"), adenosine diphosphate ("ADP"), or adenosine triphosphate ("ATP").

"Chromium" refers to trivalent chromium.

"Chromium adenosine compound" refers to a complex compound comprising chromium and an adenosine compound.

"Chromium adenosine phosphate compound" refers to a complex of chromium with an adenosine phosphate compound.

A "derivative" is a compound produced by a chemical reaction involving a parent compound.

"Metabolic disorder" refers to diabetes, diabetes-related diseases, symptoms related to diabetes, and other medical conditions involving or related to carbohydrate or lipid metabolism.

"Nucleoside sugar moiety" refers to a ribose, deoxyribose, or dideoxyribose molecule or a derivative thereof which is linked to another molecule at the 1-carbon position.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Compounds

The present compounds comprise chromium adenosine compounds, which have been found to be useful in the treatment of metabolic disorders. A complex compound comprising only chromium and adenosine has been found to be useful for such treatments, while the addition of cysteine to such a complex has been found to be even more effective. Surprisingly, such compounds have been found to have insulin-like activity.

The adenosine compound complexed with chromium in the present chromium adenosine compounds comprises an adenine moiety and a nucleoside sugar moiety. The adenine moiety preferably comprises adenine linked to a nucleic acid sugar by a linkage at the 9-nitrogen position, but can also comprise a derivative of such a moiety. Adenine moiety derivatives typically comprise an addition or substitution at the 2-carbon and/or the 8-carbon positions, such as with a hydroxy or halo moiety.

The nucleoside sugar moiety of an adenosine compound linked to such an adenine moiety at the 1-carbon position is preferably ribose or deoxyribose. The nucleoside sugar moiety can also comprise dideoxyribose, but this is less preferred as the toxicity of adenosine compounds comprising dideoxyribose is believed to be greater than for compounds comprising ribose or deoxyribose. Derivatives of such nucleoside sugar moieties can also be used. Such derivatives typically comprise an addition or substitution at the 2' and/or 3' positions of the nucleoside sugar moiety. For example, the hydroxy moiety at the 2' position of a nucleoside sugar moiety comprising ribose or deoxyribose can be substituted with an ether linkage.

In a preferred embodiment, the present compounds are chromium adenosine phosphate compounds. Preferably, the adenosine phosphate compound in such chromium adenosine phosphate compounds is AMP, ADP, or ATP, though derivatives of such moieties can also be used. Such derivatives include commercially available adenosine phosphate analogs (such as those available from BIOLOG Life Science Institute, Forschungslabor und Biochemica-Vertrieb GmbH, Flughafendamm 9a, P.O. Box 107125, -28071 Bremen, Germany) and can include, for example, 2-chloroadenosine-5'-O-triphosphate (2-Cl-ATP), 8-chloroadenosine-5'-O-triphosphate (8-Cl-ATP), adenosine-5'-O-(1-thiotriphosphate), adenosine-5'-O-(3-thiotriphosphate) (ATP-g-S), $\alpha,\beta$-methylene ATP, $\beta,\gamma$-methylene ATP, as well as 2' deoxy- and 2',3' dideoxy- versions of such compounds and mono- and di-phosphate versions of these compounds. Other alternatives such as 3',5'-cyclic adenosine monophosphate are also possible.

In a particularly preferred embodiment, the compound is a complex of chromium and ATP. Such a compound will typically comprise a molar ratio of chromium:ATP of 1:3, but complexes consisting of 1:2 and 1:1 ratios or mixtures of any of the foregoing are also possible.

In another preferred embodiment, the compound is a complex of chromium, cysteine and adenosine triphosphate. Such a compound will typically comprise a molar ratio of chromium:cysteine:ATP of 1:2:1, but complexes comprising a 1:1:1 ratio or mixtures of the foregoing are also possible. Pharmaceutically acceptable derivatives of cysteine, such as n-acetyl cysteine, can also be used in place of cysteine.

In an alternative embodiment, the present compounds comprise a complex of chromium with adenine or with a derivative of adenine. Such a complex will generally comprise chromium:adenine in a 1:3 ratio, though 1:2 and 1:1 ratios or mixtures of any of the foregoing are also possible. Adenine derivatives typically comprise an addition or substitution at the 2-carbon and/or the 8-carbon positions, as with the adenine moieties mentioned above. A chromium:adenine complex can also further include other components, such as cysteine.

Methods of Making the Compounds

Trivalent chromium salts for use in preparing the present chromium adenosine or chromium adenine compounds include any readily soluble and pharmaceutically acceptable salts, such as, for example, chromic chloride, chromic sulfate, chromic acetate, and the like. Such salts can be combined with other components of the compounds of the present invention in solution, allowed to react, and then purified.

Solvents which have been found useful in the process of the present invention include polar solvents, such as water and alcohols. It will be readily understood, however, that other polar solvents can be employed. The reactions are generally carried out at mild reaction temperatures, e.g., on the order of from about 5° C. to about 60° C., preferably from about 10° C. to about 40° C., and most preferably at approximately room temperature (approximately 25° C.). Other temperatures can be used, but the benefits in speed, yield, or purity should be balanced against any additional cost of cooling or heating the reactants.

The present compounds generally remain in solution once formed, and can be purified, for example, using ion exchange chromatography. If one of the present compounds is formed under other reaction conditions, such as at a different pH, which cause it to precipitate, such compound is preferably collected and placed into solution for further purification.

1. Chromium-ATP Complex

In a preferred embodiment, a complex of chromium and ATP is produced. In order to form such a complex, equimolar amounts of chromium and ATP are mixed in water at a pH of around 3. The mixture is then incubated at approximately room temperature for 1-2 hours to form the chromium-ATP complex. This complex is believed to have a molar ratio of chromium:ATP of approximately 1:3.

This complex can then be purified by loading 50 ml of the chromium-ATP mixture (a 10 mM solution) onto a SE53 ion-exchange column (pre-swollen, microgranular sulphoxyethyl cellulose cation ion-exchange media, available from Whatman plc, 27 Great West Road, Brentford, Middlesex, TW8 9BW, UK) having a bed volume of approximately 30 ml. The loaded column is then washed with 100 ml of water in order to wash off unbound materials. The bound chromium complex can then be eluted with 0.25 M ammonium hydroxide. The eluted fractions (4 ml/fraction) were monitored with a UV spectrophotometer for absorption at wavelengths A260 and A280.

The peak fraction (with the highest absorbance) can be collected and lyophilized. Additional chromatographic procedures can also be performed prior to lyophilization in order to further purify the chromium complex. Following purification, additional excipients can also be added to the chromium complex prior to lyophilization, for example excipients which stabilize the complex during lyophilization or which produce a pharmaceutically acceptable composition. The purified complex can also be reconstituted with a pharmaceutically acceptable carrier, such as a saline solution.

2. Chromium-Cysteine-ATP Complex

In another preferred embodiment, a complex of chromium, cysteine, and ATP is produced. In order to form such a complex, equimolar amounts of chromium, cysteine, and ATP are mixed in water at a pH of around 3. The mixture is then incubated at approximately room temperature for 1-2 hours to form the chromium-cysteine-ATP complex. A complex of chromium, cysteine, and ATP having a molar ratio of chromium:cysteine:ATP of 1:2:1 can be formed in this way.

This complex can then be purified by loading 50 ml of the chromium-cysteine-ATP mixture (a 10 mM solution) onto a SE53 ion-exchange column having a bed volume of approximately 30 ml. The loaded column is then washed with 100 ml of water in order to wash off unbound materials. The bound chromium complex can then be eluted with 0.25 M ammonium hydroxide. The eluted fractions (4 ml/fraction) were monitored with a UV spectrophotometer for absorption at wavelengths A260 and A280.

The-peak fraction (with the highest absorbance) can be collected and lyophilized. Additional chromatographic procedures can also be performed prior to lyophilization in order to further purify the chromium complex. Following purification, additional excipients can also be added to the chromium complex prior to lyophilization, for example excipients which stabilize the complex during lyophilization or which produce a pharmaceutically acceptable composition.

Pharmaceutical Compositions

In order to use the present compounds to treat a metabolic disorder, the compounds are purified so as to prepare pharmaceutically acceptable compositions. Preferably, a single species of one of the present compounds is purified for use as a pharmaceutical composition. Non-homogenous mixtures of such compounds can, however, also be used.

The present compounds can also be formulated with pharmaceutically acceptable excipients in order to create a pharmaceutical composition comprising one or more of the present compounds. A pharmaceutically acceptable excipient, including a carrier, can be chosen from those generally known in the art including, but not limited to, inert solid diluents, aqueous solutions, liposomes, microspheres, and non-toxic organic solvents, depending on the route of administration. If desired, such pharmaceutical formulations can also contain preservatives, stabilizing agents and the like, such as wetting or emulsifying agents, pH buffering agents, human serum albumin, antioxidants, preservatives, bacteriostatic agents, dextrose, sucrose, trehalose, maltose, lecithin, glycine, sorbic acid, propylene glycol, polyethylene glycol, protamine sulfate, sodium chloride, or potassium chloride, mineral oil, vegetable oils and combinations thereof. Those skilled in the art will appreciate that other excipients and carriers can also be used.

Formulations suitable for parenteral administration, such as, for example, by intravenous, intramuscular, intraperitoneal, and subcutaneous routes, include aqueous and non-aqueous isotonic sterile injection solutions. Suitable diluents and excipients include, for example, water, saline, dextrose, glycerol, or the like, and combinations thereof. These can contain solutes and other additives that render the formulation isotonic with the blood of the recipient. Alternatively, such formulations can be aqueous or non-aqueous sterile suspensions that can include suspending agents, thickening agents, and solubilizers. The pharmaceutical compositions of the present invention can be formulated for administration by any of a number of administrative routes, including intravenous infusion, oral, topical, intraperitoneal, transdermal, intranasal, intramuscular, intradermal, and subcutaneous routes.

Oral formulations can include such normally employed excipients as, for example, pharmaceutical grades of mannitol, lactose, starch, magnesium stearate, sodium saccharin, cellulose, magnesium carbonate, and the like. These compositions can contain about 1-95% of the active ingredient, and can take the form of solutions, suspensions, tablets, capsules, sustained release formulations, or powders.

Methods of Using the Compounds

Another aspect of the present invention is a method of preventing, treating and/or controlling a metabolic disorder with a pharmaceutical composition that comprises: (1) an effective amount of one or more of the present compounds; and, preferably, (2) a pharmaceutically acceptable excipient. In order to prevent, treat and/or control such conditions, an effective amount of one or more of the present compounds can be formulated as a pharmaceutical composition and administered to a human or animal subject in need thereof. A subject is determined to be in need of treatment with the present compounds through the use of standard tests for metabolic disorders, and diagnosis is generally determined by a health professional. For diabetes, diagnostic tests such as a blood glucose tests can be used to determine whether a subject is in need of treatment. A number of such tests are known to the market, for example the Assure 3 glucose meter (available from Hypoguard USA, Inc., 7301 Ohms Lane, Suite 200, Edina, Minn.).

The present compounds are administered to a patient in a quantity sufficient to prevent, treat, and/or control the symptoms and/or underlying etiology associated with diabetes or other metabolic disorder in the subject. In a preferred embodiment, the compounds are administered prior to a spike in blood glucose levels. The present compounds can also be administered in combination with other agents for controlling blood glucose levels, such as insulin. Such combined administration can comprise either a physical combination of the present compounds with another agent, or alternatively can comprise a combined therapy through the separate administration of one or more of the present compounds and another agent (in any order).

The present invention thus includes the use of the present compounds in a pharmaceutical composition to prevent, treat and/or control a metabolic disorder such as diabetes. In addition, the invention includes the use of these compounds for the manufacture of a medicament for the prevention, treatment and/or control of a metabolic disorder such as diabetes.

A therapeutically effective amount of one of the present compounds is determined using methods known to pharmacologists and clinicians having ordinary skill in the art. For example, the animal models described herein can be used to determine applicable dosages for a patient. As is known to those of skill in the art, a very low dose of a compound, i.e. one found to be minimally toxic in animals (e.g., $\frac{1}{10} \times LD10$ in mice), can first be administered to a patient, and if that dose is found to be safe, the patient can be treated at a higher dose. A therapeutically effective amount of one of the present compounds for treating a metabolic disorder can be determined by administering increasing amounts of such compound in this way to a patient suffering from such disorder until the patient's symptoms diminish or are eliminated. When the disorder is diabetes, increasing amounts of a compound can be administered until a patient achieves a desirable fasting plasma glucose level (such as between 90 mg/dl to 110 mg/dl).

Suitable dosages are also determined by taking into account such factors as the size, weight, age, and sex of the patient, the physiological state of the patient, the severity of the condition for which the compound is being administered, the response to treatment, the type and quantity of other medications being given to the patient that might interact with the compound, either potentiating it or inhibiting it, and other pharmacokinetic considerations such as liver and kidney function.

In a preferred embodiment, the present compounds have a therapeutic index of approximately 2 or greater. The therapeutic index is determined by dividing the dose at which adverse side effects occur by the dose at which efficacy for the condition is determined. A therapeutic index is preferably determined through the testing of a number of subjects.

The present compounds have been found to have insulin-like activity in treating both Type 1 and Type 2 diabetes. Approximately 100-120 μg of the present compounds (based on the weight of chromium in the compounds) has been found to have an activity equivalent to 1 International Unit (IU) of insulin (approximately 40 μg). Approximately 100 μg of a 1:2:1 complex of chromium, cysteine, and ATP has been found to have an activity of about 1 IU of insulin, while approximately 120 μg of a chromium-ATP complex have been found to have the activity of about 1 IU of insulin.

Subjects with Type 1 diabetes typically require 0.5 to 1.0 units of insulin per kilogram of body weight per day to control their diabetes. Therefore, when using the present compounds to treat Type 1 diabetes, between about 50 μg and 120 μg of one of the present compounds (based on the weight of chromium in the compound) per kilogram of body weight of a subject can be parenterally delivered to a subject in need thereof per day, with lesser and greater doses also possible. Preferably between about 50 and 120 μg of one of the present compounds per kilogram of body weight of the subject is administered. To treat and control Type 2 diabetes, similar doses can be used, though lesser doses can be indicated in mild cases of Type 2 diabetes The present compounds have been found to be orally efficacious to a greater degree than some chromium organic compounds (such as chromium picolinate). Orally administered doses of the present compounds of between approximately two and four times the effective intraperitoneal dose have a therapeutic effect. Thus, between about 1 and 10 milligrams, more preferably between 2 and 4 milligrams, of the present compounds (by weight of the chromium in the compound) can be administered to a human subject in need thereof.

If insulin is administered to the patient in addition to one of the present compounds, the dose of such compound can be decreased. The use of high doses of insulin has been associated with artherosclerosis, so the present compounds can be useful in ameliorating this side effect.

The present compounds can be delivered to a subject in any of a number of ways known to the art, including intravenous, intramuscular, intraperitoneal, subcutaneous, pulmonary, intranasal, oral, transdermal and topical administration. An effective dose for a particular route of administration can be determined as described above. As is known to those of skill in the art, the amount of a compound which is able to reach the bloodstream will vary depending on the route of administration employed. Dosing should be adjusted accordingly.

Methods of Screening Compounds

In determining the therapeutic effects and appropriate dosages of particular compounds and pharmaceutical compositions for a human or animal subject, in vitro and animal models can be used. The following models or others known to the art can be used to determine the efficacy and/or dosing of the present compounds. For example, a therapeutically effective dose can be determined by administering a range of doses of one of the present compounds to an animal which models diabetes or other metabolic disorder and then testing for, e.g., an improvement in glucose metabolism, a decrease in insulin resistance, or other indicator of improvement or control of a condition.

1. Models of Type 1 Diabetes

The standard animal model for evaluating diabetes is the Streptozotocin (STZ) model of Type I diabetes. In this model, male Sprague-Dawley rats (available from Charles River Laboratories, Inc., 251 Ballardvale Street, Wilmington, Mass.) are housed at constant room temperature (21° C.) and humidity (75%) and exposed to a 12 hour light and 12 hour dark cycle. The animals have free access to water and standard rat pellets. Experimental diabetes is then induced by intravenous injection of 65 mg Streptozotocin (STZ, available from Sigma-Aldrich, 3050 Spruce St., St. Louis, Mo.). Hyperglycemia develops in injected animals on day 2 after STZ administration. Diabetic animals are treated daily with approximately 4 IU/kg body weight of human insulin. As an alternative to STZ, high doses of other beta cell toxins like alloxan can also be used to induce Type 1 diabetes.

2. Models of Type II (Insulin-Resistant) Diabetes

A number of animal models of Type 2 diabetes exist. The sand rat (Psammomys obesus) is a model of nutritionally induced Type 2 diabetes mellitus. The fatty Zucker (ZDF) rat has hyperglycemia, early hyperinsulinemia, fasting hyperglycemia, abnormal glucose tolerance, hyperlipidemia, mild hypertension. The JCR: LA-Cp rat is a rodent model possessing insulin resistance, obesity, hypertriglyceridemia, including end stage cardiovascular diseases. Homozygous $Cpe^{fat}$ mice (Stock Number 003923, available from The Jackson Laboratory, 600 Main Street, Bar Harbor, Me.) develop a diabetic phenotype characterized by hyperglycemia and insulin resistance. A preferred mouse model is the ob/ob mouse (e.g., Strain B6.V-Lep$^{ob}$/J, available as Stock No. 000632 from The Jackson Laboratory).

3. In Vitro Models

In vitro models can also be used to evaluate the present compounds, for example, 3T3-L1 adipocytes produced as described in Example 2 below, can be used to evaluate the suitability of a compound for treating diabetes or other metabolic disorder. An increase in glucose uptake by such cells in the presence of one of the present compounds indicates that the compound is useful in treating a metabolic disorder.

EXAMPLES

Example 1A

Preparation and Purification of a Chromium-ATP Complex

Equimolar amounts of chromium chloride hexahydrate and ATP (10 mM each) were mixed in 50 ml of water at a pH of around 3. The mixture was then incubated at room temperature for 1-2 hours to form the chromium-ATP complex. This complex was purified by loading 50 ml of the 10 mM chromium-ATP mixture onto a SE53 ion-exchange column having a bed volume of approximately 30 ml. The loaded column was washed with 100 ml of water in order to wash off unbound materials. The bound chromium complex was then eluted with 0.25 M ammonium hydroxide. The eluted fractions (4 ml/fraction) were monitored with a UV spectrophotometer for absorption at wavelengths A260 and A280. The peak fraction (the one with the highest absorbance) was collected and lyophilized.

Example 1B

Preparation and Purification of a Chromium-Cysteine-ATP Complex

Figure 1:
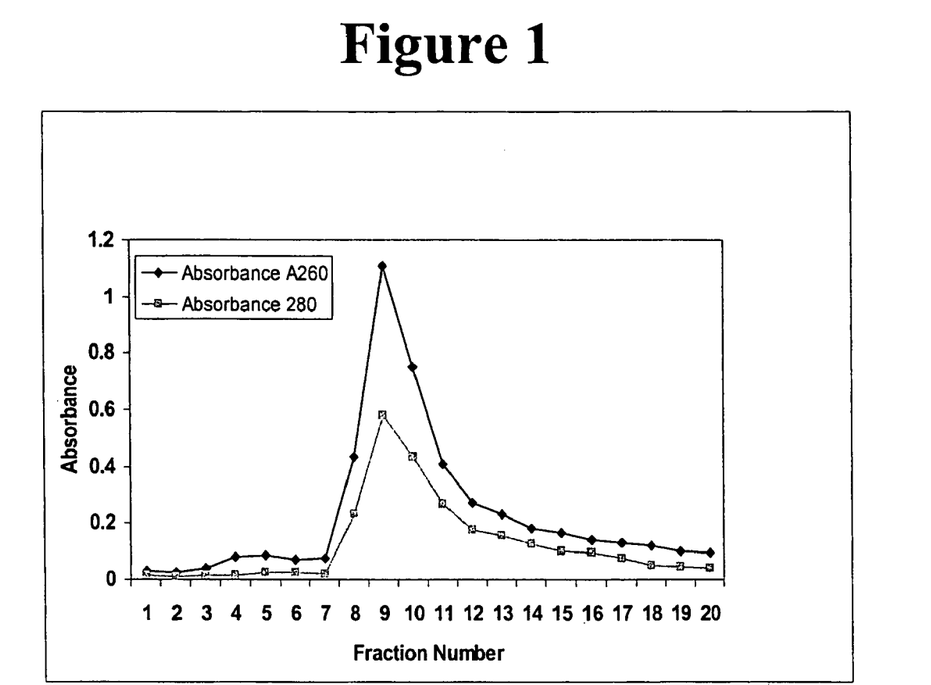
FIG. 1 is a graph showing the elution profile of the present chromium complex on a SE53 ion-exchange column.

Equimolar amounts of chromium chloride hexahydrate, cysteine, and ATP (10 mM each) were mixed in 50 ml of water at a pH of around 3. The mixture was then incubated at room temperature for 1-2 hours to form the chromium-cysteine-ATP complex. This complex was purified by loading 50 ml of the 10 mM chromium-cysteine-ATP mixture onto a SE53 ion-exchange column having a bed volume of approximately 30 ml. The loaded column was washed with 100 ml of water in order to wash off unbound materials. The bound chromium complex was then eluted with 0.25 M ammonium hydroxide. The eluted fractions (4 ml/fraction) were monitored with a UV spectrophotometer for absorption at wavelengths A260 and A280. An example of the eluting profile is shown in FIG. 1.

The peak fraction (fraction 9), with the highest absorbance, was collected and lyophilized. Chromium concentration was determined by an Inductively Coupled Plasma-Atomic Emission Spectrometer (ICP-AES). Cysteine concentration was measured with an amino acid analyzer after chemical processes of reduction, alkylation, and acid hydrolysis. ATP was analyzed with a commercial assay kit (Promega Corp., Wis.). A molar ratio of chromium:cysteine: ATP of approximately 1:2:1 was determined.

Example 2

In Vitro Testing of Chromium-Associated Compounds

The in vitro effects of various chromium-associated compounds on $^3$H-glucose uptake in 3T3-L1 adipocytes was studied using an established procedure (Siddals, K W et al., J. Endocrinology, 174:289-297 (2002)), as follows.

Cell culture. The preadipocyte 3T3-L1 cell line was obtained from the American Type Culture Collection and grown in Dulbecco's modified Eagle's medium (DMEM) Hepes modification (Sigma-Aldrich, 3050 Spruce St., St. Louis, Mo.) containing glutamine (4 mM), pyruvate (1 mM) and 10% fetal calf serum (FCS).

Differentiation of 3T3-L1 preadipocytes. 3T3-L1 preadipocytes were then seeded at a density of $5 \times 10^4$ cells/ml (day 0) and grown until 2 days post-confluent (day 8). The medium was then changed to differentiation medium (DMEM+10% FCS+glutamine and pyruvate+2 µM insulin+ 0.5 mM 3-isobutyl-L-methylxanthine+0.25 µM dexamethasone). Cells were maintained in this medium for 2 days and on day 10 the medium was changed back to normal growth medium (DMEM containing 4 mM glutamine, 1 mM pyruvate, 10% FCS and 10 nM insulin). Glucose uptake experiments were performed when more than 90% of the cells were differentiated into adipocytes.

Glucose uptake by mature 3T3-L1 adipocytes. Mature 3T3-L1 adipocytes (day 16 from plating) were serum and glucose starved for 1 hour in Hepes-buffered saline (150 mM NaCl, 5 mM KCl, 5 mMMgSO4, 1 mM CaCl2 15 mM Hepes, pH 7.2) before the addition of the test compounds, for 30 min. Glucose (2 mM 2-deoxy-glucose, 10 µCi/ml $H^3$-2-deoxyglucose, available from Amersham Biosciences Corp, 800 Centennial Avenue, P.O. Box 1327, Piscataway, N.J.) was added to each well for 15 min. Glucose uptake was then stopped by the addition of phloretin (2 mM). Adipocytes were washed with ice cold PBS and lysed in 500 µl 0 1 M NaOH. Four hundred and fifty microliters of fluid from each well were transferred into a scintillation vial and 4 ml scintillation fluid was added and counted in a β-counter for 1 min.

Figure 2:
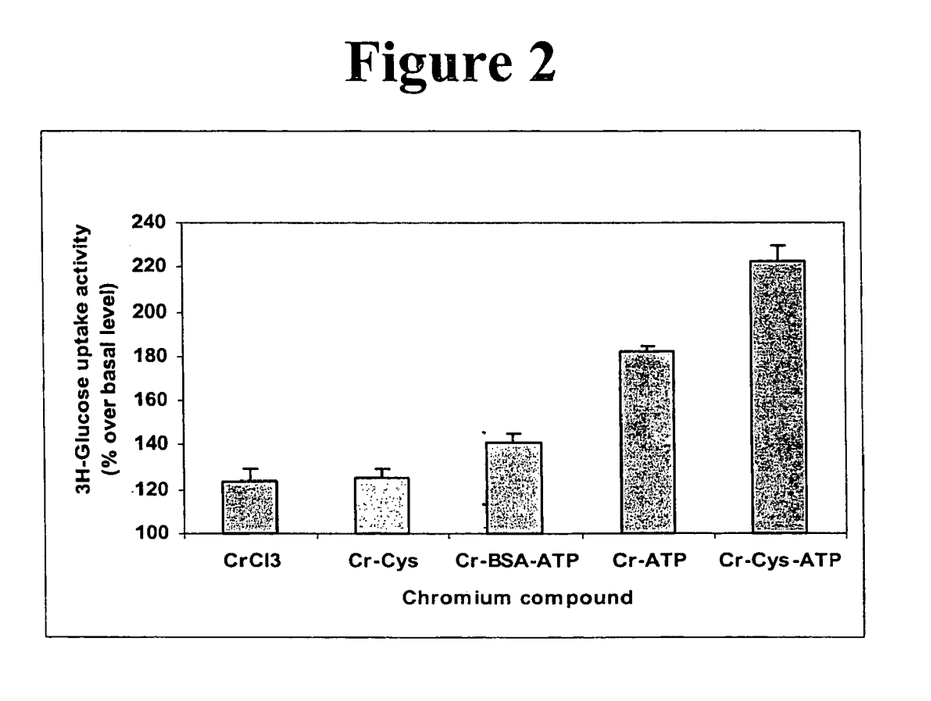
FIG. 2 is a graph showing the effects of various chromium compounds on $^3$H-glucose uptake by 3T3-L1 adipocytes.

The test compounds used in the foregoing protocol consisted of equal amounts (approximately 50 ng/ml, based on the weight of chromium in a compound) each of chromium salt ($CrCl_3$), chromium-cysteine complex, chromium-bovine serum albumin (BSA)-ATP complex, the chromium-ATP complex formed in Example 1A, and the chromium-cysteine-ATP complex formed in Example 1B. The results are summarized in FIG. 2.

Example 3

In Vitro Evaluation of Chromium-Cysteine-ATP Complex Potency

Figure 3:
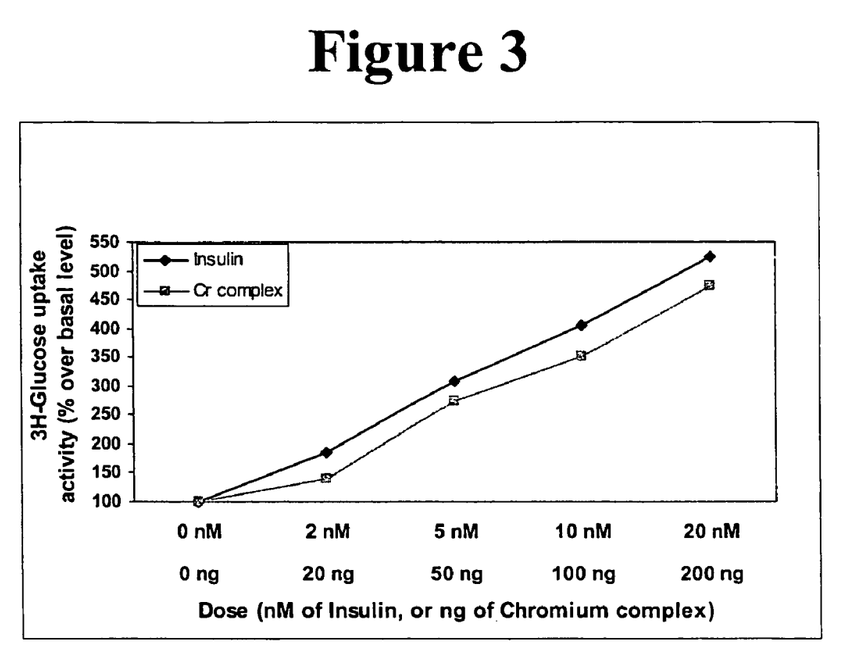
FIG. 3 is a graph showing the effects of various concentrations of the present chromium complex and insulin on the $^3$H-glucose uptake activity of 3T3-L1 adipocytes.

The in vitro potency of the chromium-cysteine-ATP complex formed in Example 1B was compared to that of human insulin. Various concentrations of this complex (0-200 ng, based on the weight of chromium in the complex, in 1 ml of medium) or insulin (0-20 nM) were used to measure the $^3$H-glucose uptake activity in adipocytes according to the protocol described in Example 2. The results are summarized in FIG. 3.

The chromium-cysteine-ATP complex demonstrated a dose-response effect parallel to that of insulin. 100 ng of the chromium complex achieved the equivalent activity of 7 nM (42 ng/ml, or 1.1 mIU/ml) of insulin.

Example 4

In Vitro Evaluation of Chromium-Cysteine-ATP Complex Activity

We studied whether the chromium-cysteine-ATP complex formed in Example 1B potentiates insulin activity or acts independently like insulin. Various concentrations of insulin (0-10 nM), with or without the addition of the 1:2:1 chromium-cysteine-ATP chromium complex of Example 1B (approximately 50 ng/ml, based on the weight of chromium in the complex), were tested to measure the $^3$H-glucose uptake activity in adipocytes according to the protocol of Example 2.

Figure 4:
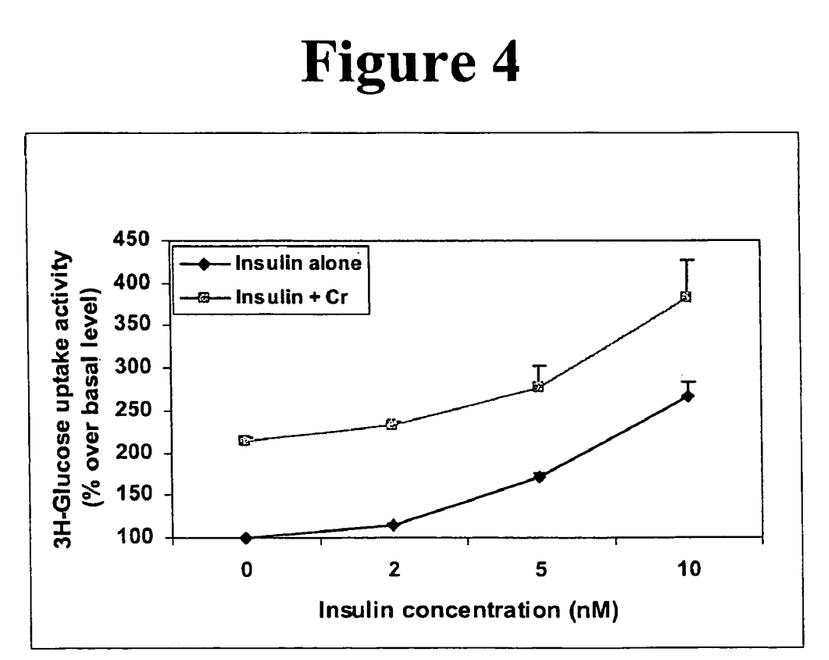
FIG. 4 is a graph showing the effects of various concentrations of insulin, with and without the addition of chromium complex, on the $^3$H-glucose uptake activity of 3T3-L1 adipocytes.

The results are summarized in FIG. 4. The parallel dose-response curves demonstrate that the addition of the chromium complex to insulin has an additive effect to the insulin activity and that the complex acts like insulin.

Example 5

In Vivo Evaluation of Chromium-Cysteine-ATP Complex Activity

Figure 5A:
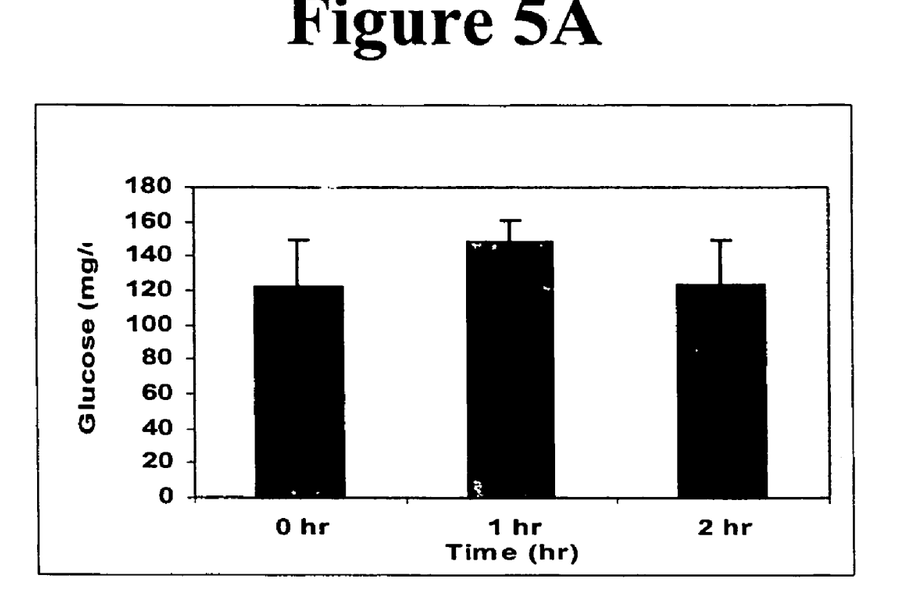
FIG. 5A is a graph showing the, effect of a saline injection on the blood sugar levels of non-diabetic mice in the study described in Example 5.
Figure 5B:
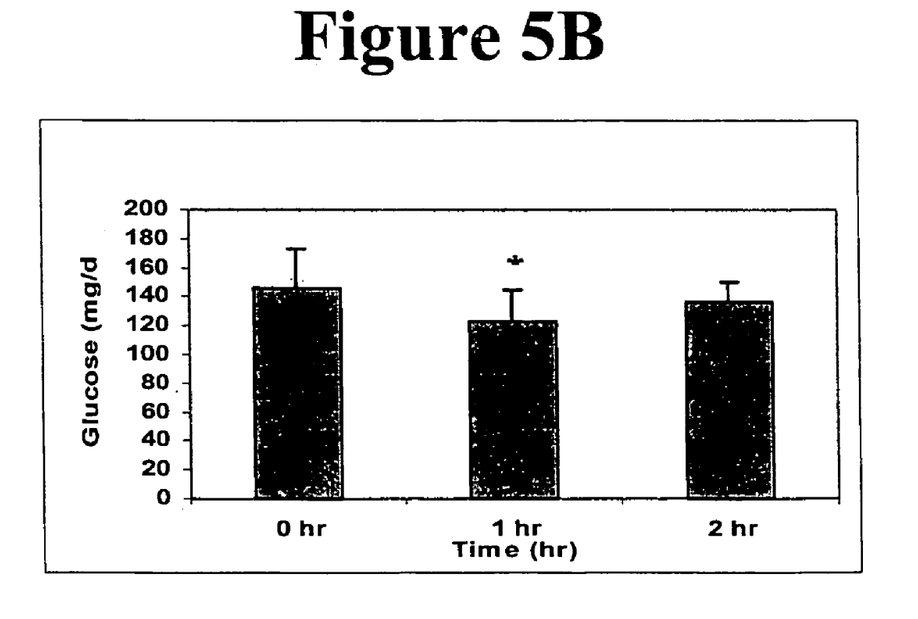
FIG. 5B is a graph showing the effect of a 1:2:1 chromium:cysteine:ATP complex on the blood sugar levels of non-diabetic mice in the study described in Example 5.
Figure 5C:
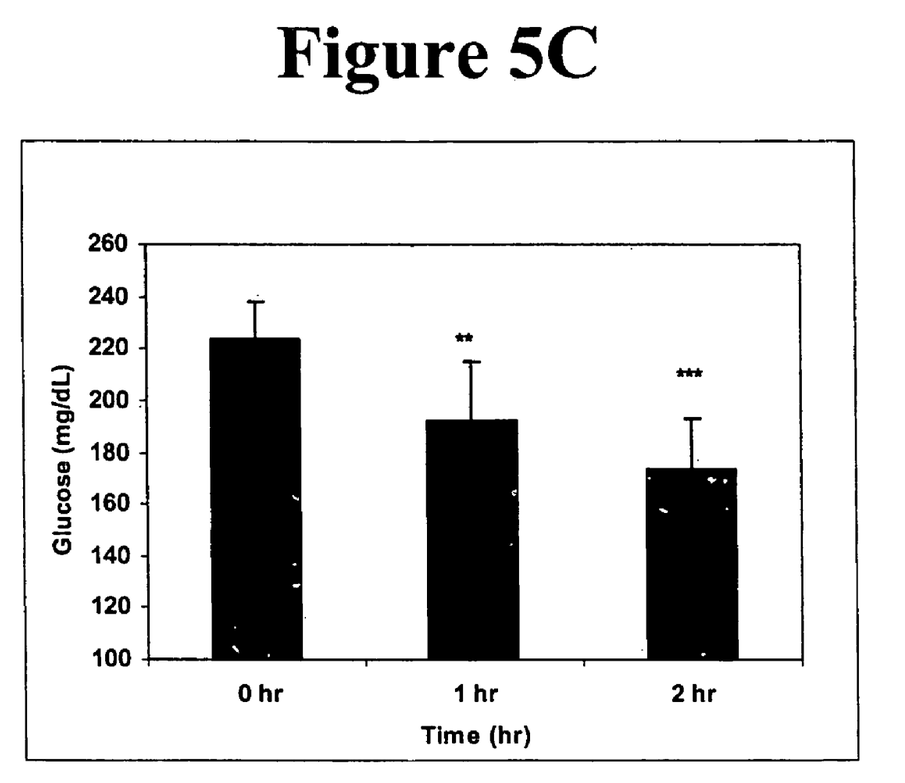
FIG. 5C is a graph showing the effect of a 1:2:1 chromium:cysteine:ATP complex on the blood sugar levels of streptozotocin-induced diabetic mice in the study described in Example 5.

The effect of the chromium complex formed in Example 1B on blood sugar levels in non-diabetic (TA1 strain) and streptozotocin-induced diabetic mice was evaluated. Two hundred μl of saline (control group) or 200 μl saline containing 0.6 or 1.2 μg of the chromium-cysteine-ATP complex (based on the weight of chromium in the complex) was injected intraperitoneally into each mouse. Blood glucose concentrations at 0 hour (pre-injection) and 1 and 2 hours post-injection were measured. The results are presented in Table 1 below and in FIGS. 5A, 5B and 5C.

TABLE 1

| Mouse Group | 0 hr (mg/dl) | 1 hr (mg/dl) (% change from 0 hr) | 2 hr (mg/dl) (% change from 0 hr) |
| --- | --- | --- | --- |
| Non-diabetic(n = 5) saline | 123 ± 27 | 149 ± 12 (+21%) | 124 ± 26 (+0.8%) |
| Non-diabetic (n = 5) 0.6 μg chromium complex | 146 ± 26 | 123 ± 22 * (−16%) | 136 ± 14 (−6.8%) |
| Diabetic mice (n = 5) 1.2 μg chromium complex | 221 ± 13 | 190 ± 20 ** (−14%) | 174 ± 16 *** (−23%) |

Note:
* p < 0.005 vs. 0 hr;
** p < 0.005,
*** p < 0.001 vs. 0 hr.

These results indicate that the chromium-cysteine-ATP complex acts like insulin in lowering blood sugar in vivo. The blood sugar decreased significantly (16% lower than at 0 hour) in non-diabetic mice 1 hour after injection with the chromium complex. In contrast, the control group showed an increase of 21% 1 hour after saline injection. The effect was even more pronounced in diabetic mice in which the blood sugar decreased 14% 1 hour after injection with the chromium-cysteine-ATP complex and further decreased to 23% by 2 hours after injection.

Example 6

Oral Administration of Chromium-Cysteine-ATP Complex

Figure 6A:
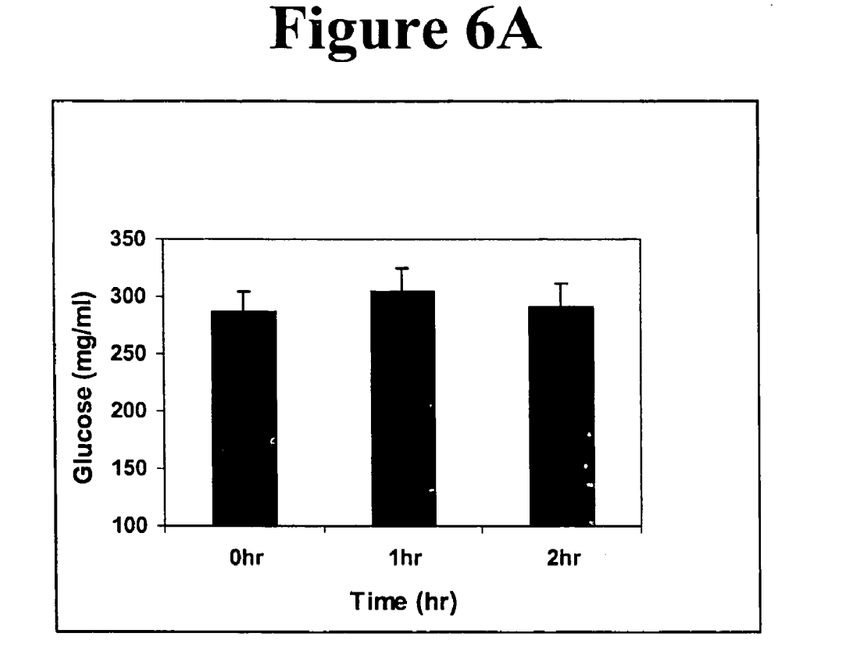
FIG. 6A is a graph showing the effect on the blood sugar levels of diabetic mice of orally administered saline in the study described in Example 6.
Figure 6B:
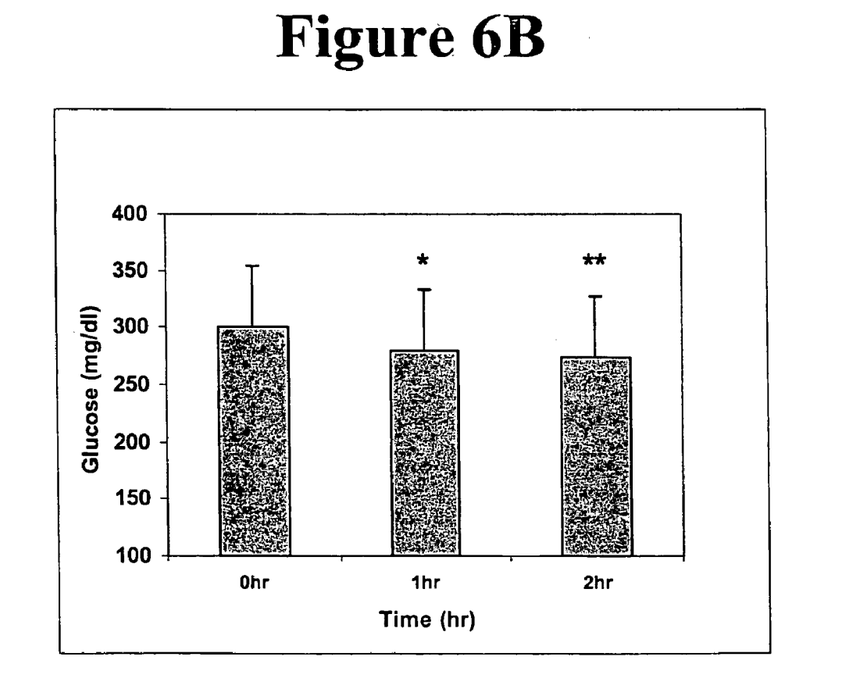
FIG. 6B is a graph showing the effect on the blood sugar levels of diabetic mice of oral administration of a 1:2:1 chromium:cysteine:ATP complex in the study described in Example 6.

The effect of orally administering the chromium-cysteine-ATP complex formed in Example 1B on blood sugar in diabetic mice (n=5) was studied. Diabetic mice were fed by mouth either with 0.25 ml of saline (control group) or with saline containing 2.4 μg of the chromium-cysteine-ATP complex (based on the weight of chromium in the complex). Blood sugar levels were measured at 0 hour (pre-feeding), and 1 and 2 hours after feeding. Oral administration of the chromium-cysteine-ATP complex effectively decreased the blood sugar levels of diabetic mice. The results are shown in Table 2 below and in FIGS. 6A and 6B.

TABLE 2

| Mouse Group | 0 hr (mg/dl) | 1 hr (mg/dl) (% change from 0 hr) | 2 hr (mg/dl) (% change from 0 hr) |
| --- | --- | --- | --- |
| Diabetic (n = 5) Saline by mouth | 286 ± 18 | 305 ± 21 (+6.6%) | 292 ± 21 (+2.1%) |
| Diabetic (n = 5) 2.4 μg chromium complex by mouth | 301 ± 52 | 279 ± 54* (−7.3%) | 273 ± 53** (−9.3%) |

Note:
*p < 0.002,
**p < 0.001 vs. 0 hr.

Example 7

Treating Type 1 Diabetes with a Chromium-Cysteine-ATP Complex

A human subject is diagnosed as having Type 1 diabetes by a physician. A pharmaceutical composition comprising a purified fraction of the chromium-cysteine-ATP complex formed in Example 1B is formulated for intravenous delivery, and 1000 μg of this complex (based on the weight of chromium in the complex) is administered to the subject.

Example 8

Treating Type 2 Diabetes with a Chromium-Cysteine-ATP Complex

A human subject is diagnosed as having Type 2 diabetes by a physician. A pharmaceutical composition comprising a purified fraction of the chromium-cysteine-ATP complex formed in Example 1B is formulated for intravenous delivery, and 1000 μg of this complex (based on the weight of chromium in the complex) is administered to the subject.

Example 9

Oral Administration of a Chromium-Cysteine-ATP Complex

A purified fraction of the chromium-cysteine-ATP complex formed in Example 1B is formulated for oral delivery. 3000 μg of this complex (based on the weight of chromium in the complex) is administered orally to a human subject diagnosed as having Type 2 diabetes.

Although the present invention has been discussed in considerable detail with reference to certain preferred embodiments, other embodiments are possible. The steps disclosed for the present methods are not intended to be limiting nor are they intended to indicate that each step depicted is essential to the method, but instead are exemplary steps only. Recitation of value ranges herein is merely intended to serve as a shorthand method for referring individually to each separate value falling within the range. Unless otherwise indicated herein, each individual value is incorporated into the specification as if it were individually recited herein.

Therefore, the scope of the appended claims should not be limited to the description of preferred embodiments contained in this disclosure. All references cited herein are incorporated by reference to their entirety.

What is claimed is:

1. A method of treating diabetes, a diabetes-related disease or symptoms related to diabetes comprising the step of administering a pharmaceutical composition comprising a therapeutically effective amount of a chromium adenosine compound to a subject in need thereof.

2. The method of claim 1, wherein the chromium adenosine compound is a chromium adenosine phosphate compound.

3. The method of claim 2, wherein the chromium adenosine phosphate compound is selected from the group consisting of AMP, ADP, and ATP.

4. The method of claim 3, wherein the chromium adenosine phosphate compound is a complex of chromium with ATP.

5. The method of claim 4, wherein the chromium adenosine phosphate compound is a complex of chromium, ATP, and cysteine.

6. The method of claim 5, wherein the molar ratio of chromium:cysteine:ATP is 1:2:1.

7. The method of claim 1, wherein the chromium adenosine compound is administered by a route selected from the group consisting of intravenous administration, intramuscular administration, intraperitoneal administration, and subcutaneous administration.

8. The method of claim 7, wherein the amount of the chromium adenosine compound administered to the subject is between about 50 µg and 120 µg of the compound per kilogram of body weight of the subject.

9. The method of claim 1, wherein the chromium adenosine compound is administered orally.

10. The method of claim 9, wherein the amount of the chromium adenosine compound administered to the subject is between about 2000 µg and 4000 µg.

11. The method of claim 1, wherein the subject has Type 1 diabetes.

12. The method of claim 1, wherein the subject has Type 2 diabetes.

13. A method of treating diabetes, a diabetes-related disease or symptoms related to diabetes comprising the step of administering to a subject in need thereof a pharmaceutical composition comprising a therapeutically effective amount of a complex of chromium with a molecule selected from the group consisting of adenine and an adenine derivative.

* * * * *